Figure 1:
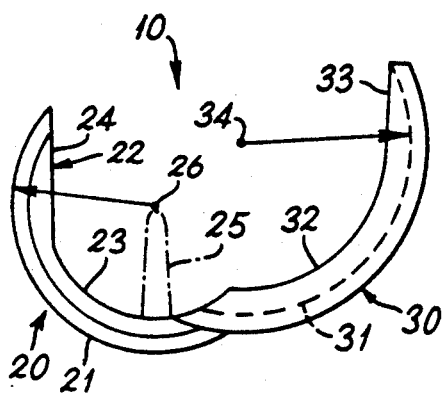

United States Patent [19]

Goodfellow et al.

[11] Patent Number: 5,226,916
[45] Date of Patent: Jul. 13, 1993

[54] PROSTHETIC FEMORAL COMPONENTS

[75] Inventors: John W. Goodfellow, Woodeaton; John J. O'Connor, Headington, both of England

[73] Assignee: British Technology Group Limited, London, England

[21] Appl. No.: 849,052

[22] PCT Filed: Aug. 28, 1991

[86] PCT No.: PCT/GB91/01446
§ 371 Date: Apr. 27, 1992
§ 102(e) Date: Apr. 27, 1992

[87] PCT Pub. No.: WO92/03108
PCT Pub. Date: Mar. 5, 1992

[30] Foreign Application Priority Data

Aug. 28, 1990 [GB] United Kingdom ............... 9018782

[51] Int. Cl.$^5$ .................................... A61F 2/38
[52] U.S. Cl. ................................... 623/20
[58] Field of Search ...................... 623/20, 18, 16

[56] References Cited

U.S. PATENT DOCUMENTS

| 3,728,742 | 4/1973 | Averill et al. | 623/20 |
| 3,806,961 | 4/1974 | Muller | 623/20 |
| 4,085,466 | 4/1978 | Goodfellow et al. | 623/20 |
| 4,094,017 | 6/1978 | Matthews et al. | 623/20 |
| 4,215,439 | 8/1980 | Gold et al. | 623/20 |
| 4,309,778 | 1/1982 | Buechel et al. | 623/20 |
| 4,340,978 | 7/1982 | Buechel et al. | 623/20 |

FOREIGN PATENT DOCUMENTS

| 2172104 | 9/1973 | France | 623/20 |
| 2465470 | 3/1981 | France | 623/20 |

Primary Examiner—Randall L. Green
Assistant Examiner—Mary Beth O. Jones
Attorney, Agent, or Firm—Cushman, Darby & Cushman

[57] ABSTRACT

A prosthetic femoral component of tricompartmental form has tibial facet surfaces (21) of like spherical shape and a patellar facet groove (31) of circular arcuate longitudinal shape, the latter having a slightly larger radius of curvature than the former, by about 1.2:R, and with the center of curvature (34) of the latter being respectively off-set by about 0.4 R and 0.6 R superiorly and anteriorly relative to those (26) of the former as seen in a lateral aspect.

9 Claims, 1 Drawing Sheet

PROSTHETIC FEMORAL COMPONENTS

This invention concerns prosthetic femoral components of tricompartmental form for replacement of the patellar facet and both tibal facets of the distal femur.

Components of this kind have been in routine use for some years, typically, although not exclusively, for total knee joint replacement in association with other components to replace the femoral facets of the proximal tibia and also the femoral facet of the patella. However, there is a current concern with the rates of failure found to arise with such other components due to various causes.

An object of the present invention is to reduce these failure rates and pursuit of this objective finds its basis in an on-going programme of development and analysis which began in the early 1970s. The first practical result of this programme was a proposal for an improved knee joint device, described in GB Patent No. 1,534,263, involving femoral, tibial and meniscal components co-operable to allow movement closely simulating that of the natural joint of flexion-extension and, at the same time, congruence at the articulation interfaces of the device. A feature of this proposal was that the femoral components could have spherically shaped tibial facets.

It has, since then, been found that the tibial facets in the natural femur in fact closely approximate spherical shaping. More recently, it has been found that the sulcus of the trochlea, the base of the patellar facet of the distal femur, closely approximates circular arcuate shaping in the sagittal plane. Most recently, it has been found that there is a sufficiently predetermined relationship between the dimensions and spacing of these shapings to allow adoption of the same in a tricompartmental femoral component.

One benefit of such a component is that it further extends the possibilities for knee joint replacement while attaining benefits similar to those of the above mentioned patent, that is to say, a capability for closer simulation of natural femoral shaping as well as close simulation of natural movement with a high degree of congruence at articulation interfaces. Another benefit is that production of such a component is facilitated by simplification of its geometry relative to prior art tricompartmental femoral components in current use whereby, when made in metal as will normally be the case, the former is more readily amenable to finish machining while the latter is usually polished directly from a cast form.

In any event, a tricompartmental femoral component according to the present invention comprises an integrated body defining two articulation surfaces of spherical shape in spaced side-by-side disposition to assume the roles of respective tibial facets, and a further articulation surface in the form of a groove extending longitudinally in off-set manner sagittally between said two surfaces to assume the role of patellar facet, said groove having circular arcuate longitudinal shape.

In terms of dimensions, the spherical shapes are preferably of the same radius of curvature as each other and the circular arcuate shape is of the same order of radius. As presently contemplated the arcuate shape will normally be of greater radius than the spherical shape by a minor proportion of the latter, suitable at about 1.2:1.

In terms of spatial relationship, the centres of the spherical shapes are coincident as seen in a lateral aspect, with the centre of the arcuate shape being relatively off-set by about 0.4 R superiorly and 0.6 R anteriorly, where R represents the radius of the spherical shapes, and the arcuate shape is essentially centrally located between the spherical shapes when viewed along a sagittal direction with the centres of the latter spaced at about 2.3 R.

The transverse cross-section of the groove may be of circular, rounded triangular or other shape to accommodate the natural patella or a patellar component.

Figure 2:
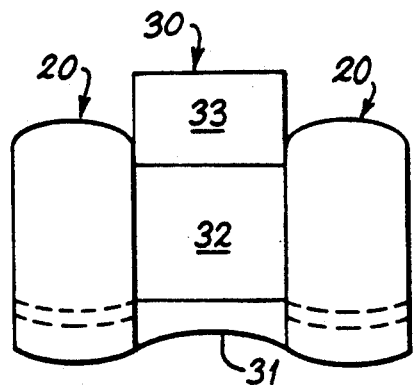
Figure 3:
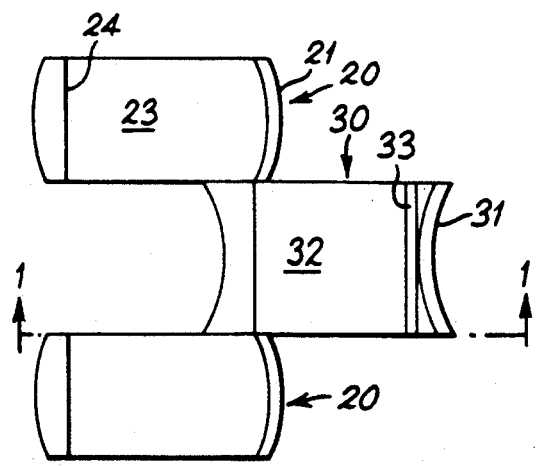

These features of the present invention are exemplified by way of an initial embodiment of the latter illustrated in the accompanying drawings, in which:

FIGS. 1, 2 and 3 diagrammatically illustrate the same respectively in a cross-section taken at 1—1 in FIG. 3, front elevation and rear elevation.

The illustrated component embodiment is denoted generally at 10 and is essentially comprised of three parts 20,30,20.

Parts 20 are of like form and correspond with unicompartmental femoral components according to Patent Specification No. GB 2215610A with each having a spherical articulation surface 21 to act as a tibial facet and a remaining surface 22 adapted for securement with bone. Surface 22 has spherical and planar portions 23,24 as taught by said Specification and may also, as indicated in broken outline in FIG. 1, have a pin 25. Parts 20 are of generally strip form disposed in spaced side-by-side manner, interconnected by way of part 30.

Part 30 is also of general strip form and it is disposed in side-by-side manner between parts 20, but off-set in a generally longitudinal sense relative to the strip forms. Part 30 is longitudinally curved in circular arcuate manner and defines a grooved articulation surface 31 on the same side of the component as surfaces 21, which surface acts as a patellar facet. This grooved surface 31 has a circular arcuate cross-sectional shape. The remaining surface 32 has a substantially cylindrical shape, although the free end portion at 33 is straightened to a planar form diverging slightly from a disposition parallel with the planar portions of surfaces 22.

In one size of this embodiment the spherical and arcuate surfaces 21 and 31 have respective radii of 24 mm and 28 mm, the respective centres 26 and 34 are spaced by 10 mm vertically and 14 mm horizontally as seen in FIG. 1, and the centres 26 are spaced by 45 mm as seen in FIG. 2. The cross-section of surface 31 has a radius of 25 mm. The divergence between surface portions 24 and 33 is about 3°.

These details relate to other dimensions proportioned essentially as illustrated, with part 30 having a width of 25 mm as seen in FIG. 2, and suit a particular size of knee. Other sizes of knee may be catered for on a simple proportionate basis. Alternatively, other sizes may involve proportionate changes only in part, to embrace the relative spacing of surfaces 21 and 31, but without corresponding changes in curvature for such surfaces.

Application of an embodiment such as illustrated can be effected by modification of the techniques proposed for a unicompartmental femoral component in the above-mentioned Specification. Certainly parts 20 can be applied in this way with femoral site preparation in the areas concerned being coordinated by way of an intramedullary nail as a reference member for the relevant tooling. Site preparation to receive part 30 can be similarly coordinated in that it involves rotary and plane cutting, suitably with end mills, of predetermined geometry relative to such a reference member.

The geometry of the embodiment is equally such that component production is facilitated. This is particularly so for the articulation surfaces which can be finish machined by simple individual rotary actions about the respective centres. This contrast with prior art tricompartmental femoral components which currently involved arcuate profiles involving three, four or more successively different curvatures which are to be smoothly blended at each curvature transition and not readily amenable to such proportion.

For the purposes of total knee joint replacement the proposed component is preferably deployed in association with tibial and meniscal components in general accordance with the above-mentioned Patent, and particularly with co-pending UK Patent Application No. 9013025.3. Also, a cooperating patellar component preferably accords with co-pending UK Patent Application No. 9018737.8.

We claim:

1. A prosthetic femoral component of tricompartmental form comprising an integrated body defining two articulation surfaces of spherical shape in spaced side-by-side disposition to assume the roles of respective tibial facets, and a further articulation surface in the form of a groove extending longitudinally in off-set manner sagittally between said two articulation surfaces to assume the role of patellar facet, said groove having circular arcuate longitudinal shape.

2. A component according to claim 1 wherein said two articulation surfaces are of the same radius of curvature and said circular arcuate shape is of the same order of radius.

3. A component according to claim 2 wherein said circular arcuate shape radius is larger than that of said two articulation surfaces by a small proportion of the latter.

4. A component according to claim 3 wherein said radii are in a ratio of about 1.2:1.

5. A component according to any one of claims 1 to 4 wherein said two articulation surfaces are coincident as seen in a lateral aspect.

6. A component according to claim 5 wherein said further articulation surface is disposed centrally between said two articulation surfaces.

7. A component according to claim 5 wherein the centre of curvature of said further articulation surface is respectively off-set by about 0.4 R and 0.6 R superiorly and anteriorly relative to the centres of curvature of said two articulation surfaces as seen in a lateral aspect, where R is the radius of curvature of said two articulation surfaces.

8. A component according to claim 5 wherein the centres of curvature of said two articulation surfaces are spaced by about 2.3 times the related radius of curvature.

9. A component according to claim 1 wherein said further articulation surface groove has a circular arcuate cross-sectional shape.

* * * * *